(12) United States Patent
Herm et al.

(10) Patent No.: US 12,187,665 B2
(45) Date of Patent: Jan. 7, 2025

(54) CROSSLINKING COMPONENT FOR BINDER RESINS

(71) Applicant: AXALTA COATING SYSTEMS IP CO., LLC, Wilmington, DE (US)

(72) Inventors: Michael Herm, Velbert (DE); Frank-Rainer Boehm, Odenthal (DE); Pascal Meiners, Muenster (DE)

(73) Assignee: AXALTA COATING SYSTEMS IP CO., LLC, Wilmington, DE (US)

(*) Notice: Subject to any disclaimer, the term of this patent is extended or adjusted under 35 U.S.C. 154(b) by 496 days.

(21) Appl. No.: 15/970,586

(22) Filed: May 3, 2018

(65) Prior Publication Data

US 2019/0337890 A1 Nov. 7, 2019

(51) Int. Cl.
| | | |
|---|---|---|
| *C07C 269/02* | (2006.01) | |
| *B05D 3/02* | (2006.01) | |
| *B05D 7/14* | (2006.01) | |
| *C07C 271/06* | (2006.01) | |
| *C07C 273/18* | (2006.01) | |
| *C07C 275/00* | (2006.01) | |
| *C09D 163/00* | (2006.01) | |
| *C09D 175/04* | (2006.01) | |
| *C08K 5/205* | (2006.01) | |
| *C08K 5/21* | (2006.01) | |

(52) U.S. Cl.
CPC .......... *C07C 269/02* (2013.01); *B05D 3/0254* (2013.01); *B05D 7/14* (2013.01); *C07C 271/06* (2013.01); *C07C 273/1854* (2013.01); *C07C 275/00* (2013.01); *C09D 163/00* (2013.01); *C09D 175/04* (2013.01); *C08K 5/205* (2013.01); *C08K 5/21* (2013.01)

(58) Field of Classification Search
CPC ............... C07C 269/02; C07C 271/06; C07C 273/1854; C07C 275/00; B05D 3/0254; B05D 7/14; C09D 163/00; C09D 175/04; C08K 5/205; C08K 5/21
See application file for complete search history.

(56) References Cited

U.S. PATENT DOCUMENTS

| | | | |
|---|---|---|---|
| 3,275,587 A * | 9/1966 | Weller | ............ C08L 63/00 523/420 |
| 4,458,056 A | 7/1984 | Holubka | |
| 2008/0152900 A1 | 6/2008 | Flosbach | |
| 2020/0339737 A1* | 10/2020 | Munzinger | ............ C08L 9/00 |

FOREIGN PATENT DOCUMENTS

| | | |
|---|---|---|
| CN | 101802042 A | 8/2010 |
| CN | 101903480 A | 12/2010 |
| CN | 104204018 A | 12/2014 |
| CN | 106147565 A | 11/2016 |

OTHER PUBLICATIONS

Frisch et al. "Polyurethanes" Comprehensive Polymer Science and Supplements vol. 5, 1989, pp. 413-426.*
Gedan-Smolka et al. "Thermal deblocking of masked low molecular isocyanates I. Aliphatic isocyanates" Thermochimica Acta 351 (2000) 95-105.*
Mohapatra et al. "Efficient and selective cleavage of the ter-butoxycarbonyl (Boc) group under basic condition" ARKIVOC, Issue 14, 2005, pp. 20-28. (Year: 2005).*
J&K Scientific "BOC Protection and Deprotection" accessed on the web at https://www.jk-sci.com/blogs/name-reaction/boc-protection-and-deprotection on May 26, 2022.*
Yuanqin Zhu, Chemistry of terminated Iso-Azonic Acid, Chemistry and Bonding, Dec. 31, 2004, Issue: No. 3.

* cited by examiner

*Primary Examiner* — Robert S Walters, Jr.
(74) *Attorney, Agent, or Firm* — Lorenz & Kopf, LLP

(57) ABSTRACT

This invention relates to a crosslinking component for binder resins which is especially suitable to be used together with epoxy-group containing binders and/or (poly)isocyanates such as blocked (poly)isocyanates and which comprises at least two blocked isocyanate groups per molecule of the crosslinking component whereby at least one of the at least two blocked isocyanate groups is a group according to structural unit (I), wherein the ratio of structural units of formula (II), if present, to structural units of formula (I) is 0.40 or below. The cross-linking component may also be self-cross-linkable. The present invention further relates to a coating composition, e.g. a one-component coating composition comprising the crosslinking component and a method of its manufacture.

7 Claims, No Drawings

CROSSLINKING COMPONENT FOR BINDER RESINS

FIELD OF THE INVENTION

This invention relates to a crosslinking component for binder resins which is especially suitable to be used together with epoxy-group containing binders and/or (poly)isocyanates such as blocked (poly)isocyanates. The cross-linking component may also be self-cross-linkable. The present invention further relates to a coating composition, e.g. a one-component coating composition comprising the cross-linking component and a method of its manufacture.

DESCRIPTION OF PRIOR ART

Melamine as crosslinker, e.g. for alkyd, acrylate or epoxy binders is known in the art. Such systems are used in coating formulations among others. However, formaldehyde may evolve from such resins during crosslinking (curing) and also after curing. In case of melamine crosslinked resins, such as coatings etc. which are in contact with the environment, the formaldehyde emission may not be recognizable by humans as the formaldehyde cannot accumulate but is diluted by the atmosphere. Moreover, due to the permanent contact with the atmosphere usually a low but continuous release of formaldehyde takes place.

In case of melamine crosslinked resins, which are not in contact with the atmosphere but are held under a protective atmosphere, e.g. in power generators or electrical engines during operation thereof, low or no release of formaldehyde takes place as long as the protective atmosphere is present. However, in case the protective atmosphere is removed, e.g. for maintenance etc., formaldehyde generation will take place leading to a delay in the start of the maintenance work or making specific equipment for the maintenance personnel mandatory leading to higher costs and also slowing down the maintenance work.

Moreover, formaldehyde generation should be reduced as far as possible due to the toxicity thereof.

In case of electrical equipment such as power generators and electrical engines a core sheet varnish (CSV) is applied to the sheets their cores are made of. These are usually one-component coating compositions based on alkyd, acrylate or epoxy binders and melamine crosslinkers.

Replacing these resins with a resin which does not generate formaldehyde is desirable. However, CSVs are applied at a low thickness while simultaneously providing good corrosion resistance and reduction of eddy currents. Moreover, the other requirements of CSVs such as appearance, flowability, punchability, weldability etc. should not be impaired.

It has been surprisingly found that using a crosslinking component comprising specific urethane groups provides good crosslinking performance while being free of formaldehyde emissions. Moreover, the crosslinking component is suitable to be used for CSVs.

Thus, the present invention provides a crosslinking component comprising at least two blocked isocyanate groups per molecule of the crosslinking component whereby at least one of the at least two blocked isocyanate groups is a group according to the following structural unit (I)

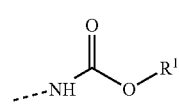

with
$R^1$ being a $C_2$ to $C_{10}$ hydrocarbyl group,
wherein
the ratio of structural units of the following formula (II), if present,

to structural units of formula (I) is 0.40 or below.

Non-aqueous, liquid coating compositions based on binders cross-linkable by blocked polyisocyanate, in particular hydroxyl-functional binders, and blocked polyisocyanate cross-linking agents are known. Examples are corresponding coating systems based on hydroxyl-functional acrylic resins (c.f. European Coatings Handbook, Curt R. Vincentz Verlag, Hannover, 2000, page 66). In such a case the blocking agent is removed and the free isocyanate is obtained which is then used to crosslink binder resins containing active hydrogen, such as polyols.

The crosslinking component of the present invention contains at least one blocked isocyanate group which forms a free amine usually by generating a C—C-double bond containing compound originating from $R^1$ and, in addition to this compound $CO_2$. The at least one further blocked isocyanate group may also be a group which forms a free amine as described above or may be a blocked isocyanate group which forms an isocyanate group upon removal of the blocking agent. In case of the latter a molecule is formed containing at least one amine and at least one isocyanate group which can undergo self-crosslinking. In case two or more amine groups are formed the crosslinking component can then be used for crosslinking reaction e.g. with resins containing epoxy groups, alpha-beta-unsaturated ester groups, (blocked) isocyanates, such as blocked (poly)isocyanates, keto groups, aldehyde groups or mixtures thereof. Moreover, coating compositions can be formed wherein the crosslinking component partially self-crosslinks and partially crosslinks a resin containing epoxy groups, alpha-beta-unsaturated ester groups, (blocked) isocyanates, such as blocked (poly)isocyanates, keto groups, aldehyde groups or mixtures thereof as mentioned above.

Moreover, formaldehyde emission cannot occur and emission of the C—C-double bond containing compound and $CO_2$ long after curing is negligible if present at all. This makes the crosslinking component particularly suitable to be used in CSVs but, of course, the crosslinking component can also be used for other applications. Moreover, due to the low content of urea groups the viscosity of the obtained coating compositions will be comparably low allowing for a higher solids content of the compositions and, thus, less solvent which needs to evaporate. In addition, a reaction of the crosslinking component of the invention with itself or a binder resin at room temperature is negligible or even does not occur at all at room temperature making the crosslinking component particularly suitable for one-component coating compositions.

SUMMARY OF THE INVENTION

This invention relates to a crosslinking component comprising at least two blocked isocyanate groups per molecule of the crosslinking component whereby at least one of the at least two blocked isocyanate groups is a group according to the following structural unit (I)

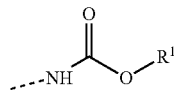

(I)

with
$R^1$ being a $C_2$ to $C_{10}$ hydrocarbyl group,
wherein
the ratio of structural units of the following formula (II), if present,

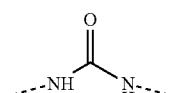

(II)

to structural units of formula (I) is 0.40 or below.

The present invention further relates to a process for producing the crosslinking component according to the invention comprising reacting a compound comprising at least two isocyanate groups with an alcohol of the formula $R^1$—OH with $R^1$ being a $C_2$ to $C_{10}$ hydrocarbyl group whereby the molar amount of the alcohol $R^1$—OH is equal to or more than the total molar amount of the compound comprising at least two isocyanate groups. Thus, at least one of the isocyanate groups of the compound comprising at least two isocyanate groups is reacted such that a structural unit according to formula (I) is formed. The other isocyanate group(s) may be reacted with an alcohol of the formula $R^1$—OH with $R^1$ being a $C_2$ to $C_{10}$ hydrocarbyl group and/or with another blocking agent.

In this context "another blocking agent" denotes a blocking agent resulting in a blocked isocyanate group which forms an isocyanate group upon removal of the blocking agent as known in the art.

The present invention further relates to a coating composition comprising the crosslinking component of the present invention.

The present invention relates to the use of the crosslinking component according to the invention for self-crosslinking and/or for crosslinking a binder resin. For example, the inventive cross-linking component may be used in one-component coating compositions or two-component coating compositions, preferably one-component coating compositions.

The present invention relates to the use of the crosslinking component according to the invention in a one-component coating composition or two-component coating composition, preferably one-component coating composition.

As explained above the crosslinking component of the invention may be self-crosslinkable.

The present invention relates to a process for crosslinking the crosslinking component according to the invention comprising the step of curing the crosslinking component.

The present invention relates to a process for crosslinking a binder resin comprising the following steps a) providing a binder resin;
b) providing a crosslinking component according to the invention;
c) combining the binder resin of step a) and the crosslinking component of step b) and optionally further components;
c1) usually and preferably applying the product obtained in step c) to a substrate and
d) curing the product obtained in step c) or step c1), if present.

DETAILED DESCRIPTION OF THE INVENTION

The invention will be explained in greater detail below.

It will be appreciated that certain features of the invention which are, for clarity, described above and below in the context of separate embodiments may also be provided in combination in a single embodiment. Conversely, various features of the invention that are, for brevity, described in the context of a single embodiment may also be provided separately or in any sub-combination. In addition, references in the singular may also include the plural (for example, "a" and "an" may refer to one, or one or more) unless the context specifically states otherwise.

Unless stated otherwise, all molecular weights (both number and weight average molecular weight) referred to herein are determined by GPC (gel permeation chromatography) using polystyrene as the standard and tetrahydrofurane as the liquid phase eluent.

The use of numerical values in the various ranges specified in this application, unless expressly indicated otherwise, are stated as approximations as though the minimum and maximum values within the stated ranges were both proceeded by the word "about." In this manner, slight variations above and below the stated ranges can be used to achieve substantially the same results as values within the ranges. Also, the disclosure of these ranges is intended as a continuous range including every value between the minimum and maximum values.

The present invention relates to a crosslinking component comprising at least two blocked isocyanate groups per molecule of the crosslinking component whereby at least one of the at least two blocked isocyanate groups is a group according to the following structural unit (I)

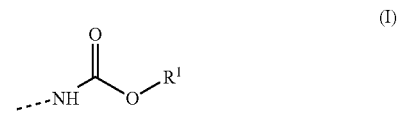

(I)

with
$R^1$ being a $C_2$ to $C_{10}$ hydrocarbyl group,
wherein
the ratio of structural units of the following formula (II), if present,

(II)

to structural units of formula (I) is 0.40 or below.

Blocked isocyanate groups which form an isocyanate group upon removal of the blocking agent are known in the art.

For the purpose of the present invention blocked isocyanate groups which form an isocyanate upon removal of the blocking agent as well as groups according to structural unit (I) are denoted "blocked isocyanate groups".

The structural units according to formula (I) are characterized in that they form an amine upon curing of the crosslinking component or coating compositions comprising the crosslinking component. As outlined above usually a compound comprising a C—C-double bond and $CO_2$ is generated thereby. Details of the curing process are given below. Curing is generally performed at a temperature of 100 to 600° C. and the curing time may range from 5 seconds to 180 min, preferably from 10 seconds to 120 minutes.

In the crosslinking component the ratio of structural units of formula (II) to structural units of formula (I)

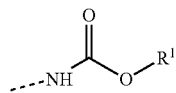
(I)

with $R^1$ being a $C_2$ to $C_{10}$ hydrocarbyl group, is 0.40 or below, preferably 0.20 or below and more preferably 0.10 or below.

In a preferred embodiment the crosslinking component is substantially free of structural units (II).

"Substantially free of structural units (II)" denotes that no compounds comprising structural unit (II) have been used during the synthesis of the crosslinking component and no structural units (II) are generated during the synthesis of the crosslinking component.

In a particular preferred embodiment the crosslinking component is free of structural units (II).

The crosslinking component is preferably free of the following structural unit (III)

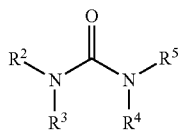
(III)

whereby none of $R^2$, $R^3$, $R^4$ and $R^5$ is a hydrogen atom.

Hence, in the crosslinking component preferably the ratio of structural units of formula (II)

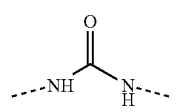
(II)

to structural units of formula (I)

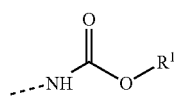
(I)

with $R^1$ being a $C_2$ to $C_{10}$ hydrocarbyl group, is 0.40 or below, preferably 0.20 or below and more preferably 0.10 or below and the crosslinking component is free of the following structural unit (III)

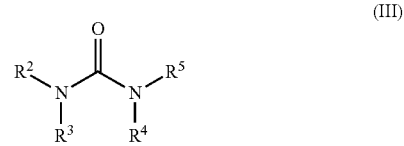
(III)

whereby none of $R^2$, $R^3$, $R^4$ and $R^5$ is a hydrogen atom.

The ratio of structural units of formula (II) to structural units of formula (I) can for instance be determined by the use of $^{13}$C-NMR spectroscopy. The carbon atoms in the carbonyl groups of formulae (I) and (II) lead to signals at different chemical shifts and thus are distinguishable in $^{13}$C-NMR. From the integrals of signals of carbon atoms of carbonyl functions in urea or urethane groups obtained in $^{13}$C-NMR, the ratio of structural units of formula (II) to structural units of formula (I) can be calculated. For this calculation, the signals in the 13C-NMR spectra must be allocated to the carbon atoms of the carbonyl function in urethane groups as present in the structural unit of formula (I) and to the carbon atoms of the carbonyl function in urea groups as present in the structural unit of formula (II). The $^{13}$C-NMR measurements may be performed in solid phase (see for instance, D. T. Okamoto et al., Macromolecules, 1992, 25 (3), pages 1068-1073) and also in liquid phase. Usually, the signal of the carbon atoms of the carbonyl function in urea groups as present in the structural unit of formula (II) is located at higher chemical shift or lower field, respectively, than the signal of the carbon atoms of the carbonyl function in urethane groups as present in the structural unit of formula (I). However, the absolute values of the chemical shifts of the signals of carbon atoms of carbonyl functions in urea or urethane groups in $^{13}$C-NMR spectra is strongly depending on the chemical nature of the surrounding groups; e.g., in case of generation of urethane and urea groups by reaction of an isocyanate group with an alcohol or amine, respectively, the chemical shifts of the signals of carbon atoms of the respective carbonyl functions in $^{13}$C-NMR spectra do not only depend on the isocyanate component, but also on the type of alcohol or amine used to generate the urethane or urea group. It might be useful, if necessary, to interpret the 13C-NMR spectra and allocate the signals with the help of $^{13}$C-NMR spectra of model compounds of known composition, e.g. which contain only urea or only urethane groups, and which resemble the structural units of formula (I) and formula (II) separately. It goes without saying that, if necessary, the skilled person may also determine the ratio of any structural units of formula (III) with the $^{13}$C-NMR based method as described above.

$R^1$ is a $C_2$ to $C_{10}$ hydrocarbyl group which may be linear, branched or cyclic, preferably branched or cyclic. $R^1$ is usually bound to the oxygen atom via a carbon atom, said carbon atom is bound to at least one further carbon atom bearing one or more hydrogen atom(s).

Non-limiting examples for $R^1$ are propyl, butyl, pentyl, hexyl, heptyl, octyl, nonyl, decyl, cyclopentyl, cyclohexyl, methylcyclopentyl, methylcyclohexyl, ethylcyclopentyl, ethylcyclohexyl including isomers thereof. Thus, for example the term "propyl" includes n-propyl as well as isopropyl and butyl includes n-butyl, sec-butyl and tert-butyl, etc.

Preferably $R^1$ is a $C_2$ to $C_{10}$ alkyl group, more preferably $R^1$ is a $C_3$ to $C_{10}$ alkyl group such as propyl, butyl, pentyl, hexyl including isomers thereof.

In a preferred embodiment $R^1$ is a butyl group. In a particular preferred embodiment $R^1$ is a tert-butyl group.

Preferably the number average molecular weight of the crosslinking component is within the range of 300 g/mol to 5000 g/mol, preferably 300 g/mol to 4000 g/mol and most preferably 300 g/mol to 3000 g/mol.

The crosslinking component of the present invention is usually produced by reacting a compound comprising at least two isocyanate groups with an alcohol of the formula $R^1$—OH with $R^1$ being a $C_2$ to $C_{10}$ hydrocarbyl group as defined above whereby the molar amount of the alcohol $R^1$—OH is equal to or more than the total molar amount of the compound comprising at least two isocyanate groups. Thus, at least one of the isocyanate groups of the compound comprising at least two isocyanate groups is reacted such that a structural unit according to formula (I) is formed. The other isocyanate group(s) may be reacted with an alcohol of the formula $R^1$—OH with $R^1$ being a $C_2$ to $C_{10}$ hydrocarbyl group as defined above and/or with another blocking agent.

In this context "another blocking agent" denotes a blocking agent resulting in a blocked isocyanate group which forms an isocyanate group upon removal of the blocking agent as known in the art.

The compound comprising at least two isocyanate groups may be a di- or polyisocyanate defined by empirical and structural formula usually having a molecular weight of not more than 800 g/mol, such as diphenylmethane diisocyanate, toluene diisocyanate (TDI), isophorone diisocyanate (IPDI), hexamethylene diisocyanate (HDI), trimers of hexamethylene diisocyanate, bis(4-isocyanatocyclohexyl)methane, bis(4-isocyanatophenyl)methane, tetramethylxylylene diisocyanate and 1,4-cyclohexane diisocyanate, bis(isocyanatocyclohexyl)-methane and their derivatives, 1,1,6,6-tetramethyl-hexamethylene diisocyanate, p- or m-tetramethylxylylene diisocyanate, 2,2',5 trimethylhexane diisocyanate, aromatic diisocyanates and their adducts, and mixtures thereof and reaction products thereof. Diphenylmethane diisocyanate, isophorone diisocyanate (IPDI), hexamethylene diisocyanate (HDI) and trimers of isophorone diisocyanate (IPDI) and hexamethylene diisocyanate are preferred.

The compound comprising at least two isocyanate groups may also be obtained by reacting a di- or polyol (A) with a di- or polyisocyanate (B).

In one embodiment the molar amount of the di- or polyisocyanate is equal to or more than the total amount of OH-groups present in the di- or polyol (A). In other words, for each of the OH-groups present in the di- or polyol at least one molecule of the di- or polyisocyanate (B) is present in the reaction.

Thus, in this embodiment each di- or polyisocyanate (B) only reacts with one of its isocyanate groups with the di- or polyol (A) while the other isocyanate group(s) is/are unchanged and can be reacted with the alcohol of the formula $R^1$—OH with $R^1$ being a $C_2$ to $C_{10}$ hydrocarbyl group in a subsequent step.

In another embodiment, when obtaining the compound comprising at least two isocyanate groups more than one of the isocyanate groups of the di- or polyisocyanate reacts with the di- or polyol (A). Thereby an oligomer or polymer may be formed.

The di- or polyol (A) may comprise polyols in the form of low molar mass compounds defined by empirical and structural formula usually having a molecular weight of up to 450 g/mol, but also oligomeric or polymeric polyols with number-average molar masses of, for example, up to about 5000 g/mol, in particular, of about 500 g/mol to about 4500 g/mol, preferably about 500 g/mol to about 3500 g/mol most preferably about 500 g/mol to about 2500 g/mol. Examples of oligomeric or polymeric polyols are corresponding hydroxyl-functional polyethers, polyurethanes, polyesters or polycarbonates.

In case the di- or polyol (A) comprise or consist of polyols in the form of low molar mass compounds defined by empirical and structural formula having a molecular weight of up to 450 g/mol, the compound preferably comprises 2 to 6, more preferably 2 to 4 and most preferably 2 to 3 OH-groups per molecule.

Examples of suitable di- or polyol (A) are ethylene glycol, the isomeric propane- and butanediols, 1,5-pentanediol, 1,6-hexanediol, 1,10-decanediol, 1,12-dodecanediol, bisphenol A, neopentyl glycol, butylethylpropanediol, the isomeric cyclohexanediols, the isomeric cyclohexanedimethanols, hydrogenated bisphenol A, tricyclodecanedimethanol, dimer fatty alcohol, glycerol, trimethylolethane and trimethylolpropane.

Examples of oligomeric or polymeric polyols are oligomeric or polymeric polyols such as telechelic (meth)acrylic polymer diols, polyester polyols, polyether polyols, polyurethane polyols, polycarbonate polyols, each with a number-average molar mass of, for example, up to about 5000 g/mol, in particular, of about 500 g/mol to about 4500 g/mol, preferably about 500 g/mol to about 3500 g/mol most preferably about 500 g/mol to about 2500 g/mol.

In one embodiment the di- or polyol (A) comprises or consists of polyols in the form of low molar mass compounds defined by empirical and structural formula having a molecular weight of up to 450 g/mol and/or oligomeric or polymeric polyurethane polyols, having a number-average molar mass of, for example, up to about 5000 g/mol, in particular, of about 500 g/mol to about 4500 g/mol, preferably about 500 g/mol to about 3500 g/mol most preferably about 500 g/mol to about 2500 g/mol.

In a preferred embodiment the di- or polyol (A) comprises or consists of polyols in the form of low molar mass compounds defined by empirical and structural formula having a molecular weight of up to 450 g/mol or oligomeric or polymeric polyurethane polyols, having a number-average molar mass of, for example, up to about 5000 g/mol, in particular, of about 500 g/mol to about 4500 g/mol, preferably about 500 g/mol to about 3500 g/mol most preferably about 500 g/mol to about 2500 g/mol.

The oligomeric or polymeric polyol preferably has a carboxyl number of about 5 to about 75 mg KOH/g, more preferably 10 to about 50 mg KOH/g and most preferably 20 to about 45 mg KOH/g.

The presence of groups which can be converted into ionic groups, such as carboxyl groups, makes the reaction product of the oligomeric or polymeric polyol and the di- or polyisocyanate (B) water soluble or water dispersible.

The oligomeric or polymeric polyol preferably has an OH number of about 50 to about 300 mg KOH/g, more preferably 100 to about 250 mg KOH/g and most preferably 150 to about 225 mg KOH/g.

Suitable polymeric polyols are described in EP 0 548 727.

Suitable polyurethane polyols are described in WO 93/01245.

Suitable di- or polyisocyanates (B) are di- or polyisocyanate defined by empirical and structural formula usually having a molecular weight of not more than 800 g/mol, such as diphenylmethane diisocyanate, toluene diisocyanate (TDI), isophorone diisocyanate (IPDI), hexamethylene diisocyanate (HDI), trimers of hexamethylene diisocyanate, bis(4-isocyanatocyclohexyl)methane, bis(4-isocyanatophenyl)methane, tetramethylxylylene diisocyanate and 1,4-cyclohexane diisocyanate, bis(isocyanatocyclohexyl)-methane and their derivatives, 1,1,6,6-tetramethyl-hexamethylene diisocyanate, p- or m-tetramethylxylylene diisocyanate, 2,2',5 trimethylhexane diisocyanate, aromatic diisocyanates and their adducts, and mixtures thereof and reaction products thereof.

In other words, one or more of the isocyanate groups of a compound comprising at least two isocyanate groups may be reacted with the alcohol of the formula $R^1$—OH with $R^1$ being a $C_2$ to $C_{10}$ hydrocarbyl group or one or more of the isocyanate groups of the di- or polyisocyanate is reacted with an oligomeric or polymeric polyol first and at least one of the remaining isocyanate group(s) are subsequently reacted with the alcohol of the formula $R^1$—OH with $R^1$ being a $C_2$ to $C_{10}$ hydrocarbyl group. The at least one further blocked isocyanate group may also be a group which forms a free amine as described above or may be a blocked isocyanate group which forms an isocyanate group upon removal of the blocking agent. In case of the latter a molecule is formed containing at least one amine and at least one isocyanate group which can undergo self-crosslinking as outlined above.

The present invention furthermore relates to a coating composition comprising the crosslinking component according to the present invention, usually further comprising a binder resin. Alternatively, the crosslinking component of the present invention may be self-cross-linkable.

As binder resins, resins crosslinkable by amine groups are preferred, such as binder resin comprising epoxy groups, alpha-beta-unsaturated ester groups, (blocked) isocyanates, such as blocked (poly)isocyanates, keto groups, aldehyde groups or mixtures thereof may be used whereby binder resins comprising epoxy groups and binder resins comprising blocked isocyanate groups are particularly preferred.

The binder resin preferably comprises, more preferably consists of a neutralized chain extended epoxy resin. Suitable epoxy resins include, for example, epoxy extended aromatic polyols, epoxy functional acrylic polymers, epoxy functional polyesters or combinations thereof. In some embodiments, the epoxy resin can be formed by the reaction product of a polyol with an epoxy compound, such as, for example, epichlorohydrin. The epoxy resin can have, on average, in the range of from 2 to 20 epoxy groups per molecule. In some embodiments, the epoxy resin can be the polyglycidyl ether of polyhydric phenols such as bisphenol A. In other embodiments, the epoxy resin can be the polyglycidyl ether of aliphatic polyols such as linear, branched or cyclic polyols. Suitable epoxy resins are known in the art and can be produced, for example, by the etherification of the polyol, e.g. polyhydric phenols and/or aliphatic polyol such as linear, branched or cyclic polyol with epihalohydrin or dihalohydrin such as epichlorohydrin or dichlorohydrin in the presence of a base.

Suitable polyols, can include polyhydric phenols, for example, 2,2-bis(4-hydroxyphenyl)propane, bis(4-hydroxyphenyl)methane, 1,2-bis-(4-hydroxyphenyl)ethane, 2-methyl-1,1-bis-(4-hydroxyphenyl)propane, 2,2-bis-(4-hydroxy-3-tertiarybutylphenyl)propane, 1,1-bis-(4-hydroxyphenol)ethane, bis-(2-hydroxynaphthyl)methane and 1,5-dihydroxy naphthalene. Besides polyhydric phenols, other cyclic polyols can be used, such as, for example, 1,2-bis (hydroxymethyl)cyclohexane, 1,3-bis-(hydroxymethyl)cyclohexane, 1,4-bis-(hydroxymethyl)cyclohexane, 1,2 cyclohexane diol, 1,3 cyclohexane diol, 1,4-cyclohexane diol and hydrogenated bisphenol A and/or aliphatic polyols, for example hexane diol and neopentyl glycol.

The molecular weight of the epoxy resin, as measured as the weight per epoxy group (wpe), can be in the range of from about 300 to about 5,000. In some embodiments the weight per epoxy is in the range of from about 400 to about 3,000, e.g. from about 450 to about 2000.

Suitable epoxy resins are known to people skilled in the art.

As the crosslinking component according to the present invention is stable at room temperature, the crosslinking component is particularly suitable for one-component coating compositions.

The coating composition of the present invention is preferably a one-component coating composition.

The concentration of the binder resin in the coating composition can be in the range of from about 1 wt. % to about 60 wt. %, based on the solids content of the coating composition.

In case a binder resin is present in the coating composition, the concentration of the crosslinking component is preferably within the range of about 10 to about 50 wt. % based on the solids content of the coating composition.

Besides the binder resin and crosslinking component described above and below, the coating composition can also contain one or more pigments which can be incorporated into the composition in the form of a pigment paste. The pigment paste can be prepared by grinding or dispersing the pigments into a grinding vehicle and other optional ingredients such as an anticrater additive, wetting agents, surfactants and defoamers. Any of the pigment grinding vehicles that are well known in the art can be used. Typically, grinding is done using conventional equipment known in the art such as, for example, an Eiger mill, Dynomill or sand mill. After grinding, the particle size of the pigment should be as small as practical, generally, the particle size is about 6 to 8 using a Hegman grinding gauge.

Pigments which can be used include, for example, titanium dioxide, barium sulfate, aluminum silicate, mixtures of silica and kaolinite, strontium chromate, carbon black, iron oxide, clay or a combination thereof. Pigments with high surface areas and oil absorbencies should be used judiciously because these can have an undesirable affect on coalescence and flow of the coating.

The weight ratio of pigment to the sum of binder resin and crosslinking component can be in the range of from about 5:1 to about 0.01:1, and in other embodiments the weight ratio of pigment to the sum of binder resin and crosslinking component can be in the range of from about 3:1 to about 0.1:1, and in further embodiments, the ratio can be in the range of from about 2:1 to about 0.1:1.

The coating compositions can contain optional ingredients such as catalysts, wetting agents, surfactants, plasticizers and defoamers. Suitable catalysts can include, for example, dialkyl tin carboxylates, such as, dibutyl tin dilaurate, dibutyl tin diacetate, dioctyl tin dicarboxylates and a combination thereof; bismuth catalysts, including, for example, bismuth oxide, bismuth trioxide, bismuth hydroxide, bismuth acetate, bismuth acetoacetonate, bismuth lactate, bismuth methane sulfate, bismuth dimethylpropionate, bismuth nitrate, zinc compounds such as zinc acetate, zinc acetylacetonate or zinc octoate, tertiary amines such as triethylamine, diazabicyclooctane (DABCO), amidines such as diazabicycloundecene (DBU) or diazabicyclononene (DBN), and a combination thereof. Combinations of any of the catalysts can also be used. Examples of surfactants and wetting agents include, for example, alkyl imidazolines such as those available from Ciba-Geigy Industrial Chemicals as AMINE® C, acetylenic alcohols available from Air Products and Chemicals as SURFYNOL® 104. Examples of useful plasticizers can be water immiscible materials such as ethylene or propylene oxide adducts of nonyl phenols or bisphenol A. These optional ingredients, when present, constitute in the range of from about 0.1 to about 20 percent by weight based on the solids content of the coating composition. In case these optional ingredients are present, the sum of crosslinking component, binder resin and pigments, if present is 99.9 to 80 wt. % based on the solids content.

The total amount of binder resin, crosslinking component, pigments, if present, and optional ingredients, if present is 100 wt. % based on the solids content of the coating composition.

The coating composition is preferably an electrical insulation material, more preferably a core sheet varnish (CSV).

A core sheet varnish (CSV) is used for electrical steel intended for motors and generators. The rotor and/or stator of electrical motors and generators comprises stacks of metal sheets, usually electrical steel sheets, which are coated with a composition, preferably with the coating composition of the present invention.

Preferred embodiments of the cross-linking component according to the present invention are also preferred embodiments of the coating composition according to the present invention and vice versa.

The present invention furthermore relates to the use of the crosslinking component according to the present invention for crosslinking a binder resin and/or for self-crosslinking.

The binder resin may be selected from the binder resins defined above. In a preferred embodiment the binder resin is selected from the binder resins defined above. In a particularly preferred embodiment the binder resin is a binder resin comprising epoxy and/or blocked isocyanate groups.

The present invention is furthermore directed to the use of the crosslinking component according to the invention in a two-component coating composition or one-component coating composition, preferably one-component coating composition.

Preferred embodiments of the cross-linking component and the coating composition according to the present invention are also preferred embodiments of the uses according to the present invention and vice versa.

The present invention relates to a process for crosslinking the crosslinking component according to the invention or a coating composition comprising the crosslinking component according to the invention comprising the step of curing the crosslinking component according to the invention or the coating composition comprising the crosslinking component according to the invention. Usually and preferably the crosslinking component according to the invention or the coating composition comprising the crosslinking component according to the invention is applied to a substrate prior to curing.

The present invention is furthermore directed to a process for crosslinking a binder resin comprising the following steps
  a) providing a binder resin;
  b) providing a crosslinking component according the invention;
  c) combining the binder resin of step a) and the crosslinking component of step b) and optionally further components;
  c1) usually and preferably applying the product obtained in step c) to a substrate; and
  d) curing the product obtained in step c) or step c1), if present.

The binder resin may be selected from the binder resins defined above. In a preferred embodiment the binder resin is selected from the binder resins defined above. In a particularly preferred embodiment the binder resin is a binder resin comprising epoxy and/or blocked isocyanate groups.

The optional further components are usually selected from the compounds defined above for the coating composition. The optional further components are usually present in an amount of not more than 15 wt. % based on the resin solids, preferably not more than 10 wt. % of the resin solids.

The substrate is not particularly limited and may, for example be metal, glass, or a polymer. Metallic substrates are preferred whereof steel sheets are particularly preferred. Most preferred are electrical steel sheets.

Generally the curing temperature may range from 100 to 600° C. and the curing time may range from 5 seconds to 180 minutes, preferably 10 seconds to 120 minutes. As known to the skilled person the curing time is shorter at higher temperature and vice versa. For example, in case of polymeric substrates longer curing times at lower temperatures may be needed.

The necessary heat for curing can be supplied, for example, in an oven, by means of induction heating, infrared (IR) radiation, near infrared (NIR) radiation and/or hot air.

In one embodiment the curing temperatures can be, for example, in the range of 200 to 600° C., preferred 300 to 450° C., in a time period of 5 seconds to 1 minute.

In another embodiment the curing temperatures can also be, for example, in the range of 100 to 300° C., in a time period of, for example, 60 to 180 minutes.

The crosslinking of the coating on steel sheets preferably takes places by thermal curing under definite curing conditions, preferably, at temperatures providing a PMT (peak metal temperature) in the range of 180 to 260° C., preferably 230 to 260° C.

The means for combining the compounds in step c) are known in the art.

Usually the components are combined in step c) at a temperature of below 80° C., preferably below 50° C., more preferably within the range of 0 to 50° C. In a preferred embodiment the components are combined in step c) at a temperature of 10 to 30° C.

The structural units (I) of the cross-linking component undergo thermal decomposition releasing an alkene and carbon dioxide and yielding an amine. Cross-linking is then accomplished via the amine groups.

Preferred embodiments of the cross-linking component, the coating composition and the uses according to the present invention are also preferred embodiments of the process according to the present invention and vice versa.

The invention claimed is:
1. A coating composition comprising a crosslinking component comprising at least two blocked isocyanate groups per molecule of the crosslinking component whereby at least one of the at least two blocked isocyanate groups is a group according to the following structural unit (I)

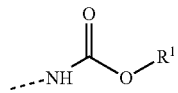

(I)

with
$R^1$ being a $C_2$ to $C_{10}$ hydrocarbyl group,
wherein
the ratio of structural units of the following formula (II), if present,

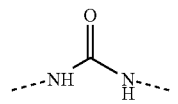

(II)

to structural units of formula (I) is 0.20 or below; and
a binder resin comprising epoxy groups, alpha-beta-unsaturated ester groups, (blocked) isocyanates, keto groups, aldehyde groups or mixtures thereof;
where the structural unit (I) forms a free amine by generating a C—C double bond containing compound originating from $R_1$ and $CO_2$ during reaction with the resin.

2. The coating composition according to claim 1 wherein the crosslinking component is substantially free of structural units (II).

3. The coating composition according to claim 1 wherein $R^1$ is a $C_2$ to $C_{10}$ alkyl group.

4. The coating composition according to claim 1 wherein $R^1$ is a tert-butyl group.

5. The coating composition according to claim 1 wherein the number average molecular weight of the crosslinking component is within the range of 350 g/mol to 5000 g/mol.

6. The coating composition of claim 1 wherein the binder resin is a binder resin comprising epoxy and/or blocked isocyanate groups.

7. The coating composition of claim 1 being a one-component coating composition.

* * * * *